United States Patent [19]

Winkelmann et al.

[11] 4,001,415
[45] Jan. 4, 1977

[54] COMPOSITION FOR AND METHOD OF TREATING DISEASES CAUSED BY PROTOZOA

[75] Inventors: Erhardt Winkelmann, Kelkheim, Taunus; Wolfgang Raether, Dreieichenhain, Germany

[73] Assignee: Hoechst Aktiengesellschaft, Frankfurt am Main, Germany

[22] Filed: Sept. 4, 1975

[21] Appl. No.: 610,459

Related U.S. Application Data

[62] Division of Ser. No. 476,990, June 6, 1974, Pat. No. 3,905,985.

[30] Foreign Application Priority Data

June 8, 1973  Germany ............................ 2329376

[52] U.S. Cl. ............................................... 424/263
[51] Int. Cl.² ...................................... A61K 31/44
[58] Field of Search ................................. 424/263

[56] References Cited

UNITED STATES PATENTS

| | | | |
|---|---|---|---|
| 3,635,995 | 1/1972 | Manning | 260/294.8 |
| 3,905,985 | 9/1975 | Winkelmann et al. | 424/263 |
| 3,922,277 | 11/1975 | Winkelmann et al. | 424/263 |
| 3,929,807 | 12/1975 | Fitzi | 424/263 |

*Primary Examiner*—V. D. Turner
*Attorney, Agent, or Firm*—Curtis, Morris & Safford

[57] ABSTRACT

New 1-alky-2-(pyridyl-sulfinylmethyl)-5-nitro-imidazoles and 1-alkyl-2-(pyridyl-sulfonylmethyl)-5-nitro-imidazoles are described according to the formula I

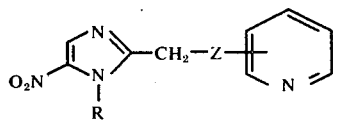

in which R stands for a methyl, ethyl or hydroxyethyl group and Z stands for a —SO— or —SO₂— group and the pyridine ring is linked to the sulfinyl or the sulfonyl group in 2, 3 or 4 position as well as a process for their manufacture.

The novel compounds have a pronounced activity against protozoae, especially trichomonads and amebae.

6 Claims, No Drawings

COMPOSITION FOR AND METHOD OF TREATING DISEASES CAUSED BY PROTOZOA

This is a division of application Ser. No. 476,990, filed June 6, 1974, now U.S. Pat. No. 3,905,985 granted Sept. 16, 1975.

The present invention relates to 1-alkyl-2-(pyridylsulfinylmethyl)-5-nitro-imidazoles and to 1-alkyl-2-(pyridylsulfonylmethyl)-5-nitro-imidazoles and a process for their manufacture.

1-(2'-hydroxyethyl)-2-methyl-5-nitroimidazole (Metronidazol) is known to be used for the treatment of protozoal diseases, such as trichomoniasis and amebiasis.

Object of this invention are 1-alkyl-2-(pyridylsulfinylmethyl)-5-nitro-imidazoles and 1-alkyl-2-(pyridylsulfonylmethyl)-5-nitro-imidazoles of the formula I

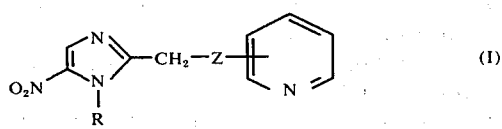

in which R stands for a methyl, ethyl or hydroxyethyl group and Z stands for a —SO— or —SO$_2$— group and the pyridine ring is linked to the sulfinyl or the sulfonyl group in 2, 3 or 4 position.

The novel compounds have a pronounced activity against trichomonads and amebae, which activity is superior to the said Metronidazol.

Further object of this invention is a process for the manufacture of 1-alkyl-2-(pyridylsulfinylmethyl)-5-nitro-imidazoles and 1-alkyl-2-(pyridylsulfonylmethyl)-5-nitro-imidazoles of the formula I which process comprises oxidizing 1-alkyl-2-(pyridylthiomethyl)-5-nitroimidazoles of the formula II

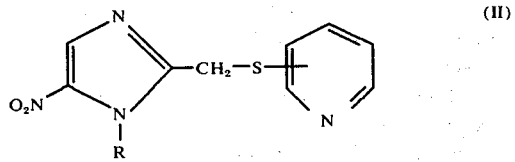

in which R is defined as above.

The 1-alkyl-2-(pyridylthiomethyl)-5-nitroimidazoles of the formula II can be obtained, for example, by reacting 1-alkyl-2-halogenomethyl-5-nitroimidazoles of the formula III

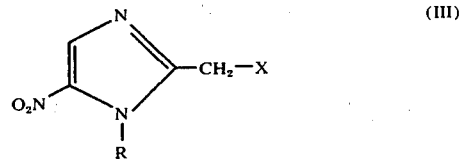

in which R is defined as above and X stands for a halogen atom or an arylsulfonic acid ester grouping, especially phenyl sulfonic acid or tolylsulfonic acid, with mercaptopyridines of the formula IV

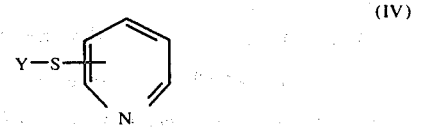

in which Y stands for a hydrogen atom or an alkali metal or ammonium ion in an aprotic solvent, such as xylene or dimethyl acetamide at elevated temperature. The 1-alkyl-2-chloromethyl-5-nitroimidazoles of the formula III can themselves be obtained by reacting 1-alkyl-2-hydroxymethyl-5-nitroimidazoles with thionyl chloride.

The oxidation reactions are advantageously carried out by using once or twice the molar amount of an oxidizing agent. When treating the sulfides with a mol equivalent of the oxidizing agent, sulfoxides are obtained, the treatment with two mol equivalents of oxidizing agent yields sulfones. Suitable oxidizing agents are, for example, hydrogen peroxide or per acids, such as, for example, peracetic acid, pertrifluoroacetic acid or metachloroperbenzoic acid as well as nitric acid or chromic acid or the salts thereof, moreover, permanganates, hypochlorites, perchlorates, periodates and nitrogen oxide.

The oxidation reactions are advantageously carried out in a solvent or a dispersion agent. In this case, especially suitable solvents are those which are not attacked by the oxidizing agent, such as, for example, acetic acid, trifluoroacetic acid. When perbenzoic acid is used, methylene chloride or chloroform can also be used as solvents.

The oxidation reactions which are to lead to the sulfinyl compounds, are generally carried out at a temperature ranging from 10° to 30° C. The sulfonyl compounds are generally obtained at oxidation temperatures ranging from 50° to 100° C. Optionally the sulfonyl compounds may also be manufactured by oxidizing the corresponding sulfinyl compounds with the oxidizing agents mentioned at elevated temperature.

Depending on the mode of operation and the final product desired, the reaction times are in the range of from a few minutes to several hours.

The products of the invention are isolated by diluting the reaction solution with water and simultaneously precipitating or evaporating the organic solvent under reduced pressure. Optionally, the products can be purified by recrystallization from a suitable solvent or mixture of solvents.

The 1-alkyl-2-(pyridylsulfinylmethyl)-5-nitro-imidazoles and 1-alkyl-2-(pyridylsulfonylmethyl)-5-nitro-imidazoles of the formula I are suitable for the treatment of protozoal diseases in mammals, for example, those diseases caused by infections with *Trichomonas vaginalis* and *Entamoeba histolytica*. The novel products of the invention may be administered by the oral or local route. For the oral administration, the products are generally made into tablets or capsules containing, per daily dosage unit, about 10 to 750 mg of the active ingredient, in admixture with a usual diluent and/or excipient. For a local application, jellies, creams, ointments or suppositories may be used.

In addition to a good commpatibility, the compounds of the invention are distinguished by a safe activity against trichomonads and amebae in vivo, which activity is substantially superior to the known pharmaceutical composition Metronidazol, as can be seen from the following Tables.

The following Examples illustrate the invention.

EXAMPLE 1 (test for activity)

Activity against *Trichomonas foetus* was generally tested on home-bred albino mice (NMRI-strain) of both sexes. The body weight of each animal was from 10 to 12 grams.

The substance to be tested was administered orally by means of an oesophagal sound either in an aqueous solution or, in the case of sparingly water-soluble compounds, in a Tylose suspension. The overall dosage was administered in two units, the first two hours prior to infection and the second two hours after infection. 4 Mice were used for each substance to be tested and for each dosage.

Infection was brought about by intraperitoneal injection of 19 million infective agents per animal in a suspension in 0.5 ml of a culture medium, Merck I. The comparison preparation Metronidazol was administered by the same route and in the same dosage as the substance to be tested (see Table 1).

As infection controls there were generally used 10 mice which, after infection, were not treated any more. Another 5 mice served as a zero control, that is to say, these animals were neither treated nor infected.

Six days after infection, all the test animals were killed and the peritoneal exudate was examined for trichomonads. Mice which died before were subjected to the same examination.

The tested substance ws judged on the concentration of infective agents to be found in the peritoneal exudate on the 6th day after infection. For this purpose, the concentration of infective agents established with the tested composition was compared with that of the comparison preparation and of the infection control. The scheme, according to which the tested substance and the standard were judged with regard to the concentration of infectants established, was the following:

ineffective:
Concentration of infective agents was not substantially reduced as compared to infection control. Judgement: 3; 4 effective:
a. faint: Concentration of infective agents was moderately reduced compared with infection control. Judgement: 2 b. unsatisfactory: Concentration of infective agents was substantially reduced compared with infection control. Judgement: 1 c. no infective agents found. Judgement: 0

TABLE 1

| Composition | dosage in mg/kg mouse, per os | concentration of infectant Trichomonas foetus in 4 mice |
|---|---|---|
| I | 2 × 100 | 0 0 0 0 |
|  | 2 × 50 | 0 0 0 0 |
|  | 2 × 25 | 0 0 0 0 |
|  | 2 × 12.5 | 0 0 0 0 |
| II | 2 × 100 | 0 0 0 0 |
|  | 2 × 50 | 0 0 0 0 |
|  | 2 × 25 | 1 0 2 2 |
|  | 2 × 12.5 | 4 3 4 3 |
| infection control | — | 4 4 4 4 |

I = product of the invention: 1-methyl-2-(2-pyridylsulfonyl-methyl)-5-nitroimidazole
II = comparative composition: Metronidazol

EXAMPLE 2 (test for activity)

Activity against *Entamoeba histolytica* was generally tested on cross-bred golden hamsters of both sexes. The body weight of each animal was generally in the range of from 50 to 60 grams.

The substance to be tested was administered orally by means of an oesophagal sound, either in an aqueous solution or, in the case of sparingly water-soluble compounds, in a Tylose suspension. The overall dosage was administered in four units, the first two hours prior to infection, the second two hours after infection, the third one day after infection and the fourth two days after infection. 4 Hamsters were used for each substance to be tested.

Infection was brought about by intrahepatic injection of 130,000 infective agents per animal as a suspension in 0.1 ml of TTY medium (E. hist.-Crithidia culture). The standard Metronidazol was administered by the same route and in the same dosage as the substance to be tested (see Table 2).

As infection controls there were generally used 10 hamsters which were, after infection, not treated any more. Another 5 hamsters served as a zero control, that is to say, these animals were neither treated nor infected.

Six days at the earliest and eight days at the latest after infection, all the animals were killed. Subsequently, the state of the liver was judged according to the degree of icteric necrosis developed. Hamsters which had died during the period of infection were subjected to the same examination.

The observations on the state of the liver obtained with the tested composition and with the standard were compared with those of the infection controls. The scheme, according to which the liver findings (with tested composition and standard) were judged, was the following:

ineffective:
Icteric necrosis did not show any substantial difference from that of infection controls. Possible judgement: 3; 4 (in rare cases: 2), effective:
a. faint: Icteric necrosis was less developed than with the infection controls. Possible judgement:
frequently 2 (in rare cases: 1), b. unsatisfactory: Icteric necrosis was substantially reduced as compared to infection controls. Possible judgement:
0 (in rare cases), predominantly 1;
2 (in rare cases), c. good: no icteric necrosis was discovered. Judgement: 0

TABLE 2

| composition | dosage in mg/kg golden hamster, per os | liver findings Entamoeba histolytica (extraintestinal) in 4 golden hamsters |
|---|---|---|
| I | 4 × 100 | 0 0 0 0 |
|  | 4 × 50 | 0 0 0 0 |
|  | 4 × 25 | 0 0 0 0 |
| II | 4 × 100 | 0 0 0 0 |
|  | 4 × 50 | 0 1 0 1 |
|  | 4 × 25 | 2 0 2 3 |
| infection | — | 4 4 3 4 |

TABLE 2-continued

| composition | dosage in mg/kg golden hamster, per os | liver findings Entamoeba histolytica (extraintestinal) in 4 golden hamsters |
|---|---|---|
| controls | | |

I = Product of the invention: 1-methyl-2-(2-pyridylsulfonylmethyl)-5-nitroimidazole
II = comparative composition: Metronidazol EXAMPLE 3 (preparation of active substance):

1.  1-Methyl-2-(2-pyridylsulfonylmethyl)-5-nitroimidazole 25.0 g (0.1 mol) of 1-methyl-2-(2-pyridylthiomethyl)-5-nitro-imidazole were dissolved in 400 ml of acetic acid and 20.0 ml (0.2 mol) of 35 % hydrogen peroxide were added drop-wise at room temperature while stirring. There is no exothermic reaction. Then, the solution was stirred on the steam bath for 2 hours while heating. The reaction solution was evaporated under reduced pressure and the residue was recrystallized from water/alcohol.

Thus, 24.0 g of 1-methyl-2-(2-pyridylsulfonylmethyl)-5-nitro-imidazole (corresponding to 85 % of the theory) were obtained in the form of yellowish crystals which melted at 187° C.

In an analogous manner, there were obtained with good yields, 2. 1-Methyl-2-(3-pyridylsulfonylmethyl)-5-nitroimidazole from 1-methyl-2-(3-pyridylthiomethyl)-5-nitroimidazole.

3. 1-Methyl-2-(4-pyridylsulfonylmethyl)-5-nitroimidazole (m.p. 191° C) from 1-methyl-2-(4-pyridylthiomethyl)-5-nitroimidazole.

4. 1-Ethyl-2-(2-pyridylsulfonylmethyl)-5-nitroimidazole from 1-ethyl-2-(2-pyridylthiomethyl)-5-nitroimidazole.

5. 1-Ethyl-2-(3-pyridylsulfonylmethyl)-5-nitroimidazole from 1-ethyl-2-(3-pyridylthiomethyl)-5-nitroimidazole.

6. 1-Ethyl-2-(4-pyridylsulfonylmethyl)-5-nitroimidazole from 1-ethyl-2-(4-pyridylthiomethyl)-5-nitroimidazole.

7. 1-(2-hydroxyethyl)-2-(2-pyridylsulfonylmethyl)-5-nitroimidazole from 1-(2-acetoxyethyl)-2-(2-pyridylthiomethyl)-5-nitroimidazole after saponification of the acetyl group.

8. 1-(2-hydroxyethyl)-2-(3-pyridylsulfonylmethyl)-5-nitroimidazole from 1-(2-acetoxyethyl)-2-(3-pyridylthiomethyl)-5-nitro-imidazole after saponification of the acetyl group.

9. 1-(2-hydroxyethyl)-2-(4-pyridylsulfonylmethyl)-5-nitroimidazole from 1-(2-acetoxyethyl)-2-(4-pyridylthiomethyl)-5-nitroimidazole after saponification of the acetyl group.

10. 1-Methyl-2-(2-pyridylsulfinylmethyl)-5-nitroimidazole 25.0 g (0.1 mol) of 1-methyl-2-(2-pyridylthiomethyl)-5-nitroimidazole were dissolved in 200 ml of chloroform and 17.25 g (0.1 mol) of m-chloroperbenzoic acid, dissolved in 50 ml of chloroform, were added dropwise at room temperature. The reaction solution was then stirred for another hour at room temperature, extracted with dilute sodium carbonate solution, the chloroform phase was separated, dried over sodium sulfate and evaporated. The residue was recrystallized from alcohol.

Thus, 21.0 g of 1-methyl-2-(2-pyridylsulfinylmethyl)-5-nitro-imidazole (79 % of the theory) were obtained in the form of yellowish crystals which melted at 160° C.

In an analogous manner, there were obtained in good yields, 11. 1-Methyl-2-(3-pyridylsulfinylmethyl)-5-nitroimidazole from 1-methyl-2-(3-pyridylthiomethyl)-5-nitroimidazole.

12. 1-Methyl-2-(4-pyridylsulfinylmethyl)-5-nitroimidazole (m.p. 163° C) from 1-methyl-2-(4-pyridylthiomethyl)-5-nitroimidazole.

13. 1-Ethyl-2-(2-pyridylsulfinylmethyl)-5-nitroimidazole (m.p. 82° C) from 1-ethyl-2-(2-pyridylthiomethyl)-5-nitroimidazole.

14. 1-Ethyl-2-(3-pyridylsulfinylmethyl)-5-nitroimidazole from 1-ethyl-2-(3-pyridylthiomethyl)-5-nitroimidazole.

15. 1-Ethyl-2-(4-pyridylsulfinylmethyl)-5-nitroimidazole from 1-ethyl-2-(4-pyridylthiomethyl)-5-nitroimidazole.

16. 1-(2-hydroxyethyl)-2-(2-pyridylsulfinylmethyl)-5-nitroimidazole from 1-(2-acetoxyethyl)-2-(2-pyridylthiomethyl)-5-nitroimidazole after saponification of the acetyl group.

17. 1-(2-hydroxyethyl)-2-(3-pyridylsulfinylmethyl)-5-nitroimidazole from 1-(2-acetoxyethyl)-2-(3-pyridylthiomethyl)-5-nitroimidazole after saponification of the acetyl group.

18. 1-(2-hydroxyethyl)-2-(4-pyridylsulfinylmethyl)-5-nitroimidazole from 1-(2-hydroxyethyl)-2-(4-pyridylthiomethyl)-5-nitroimidazole after saponification of the acetyl group.

The 1-alkyl-2-(pyridylthiomethyl)-5-nitroimidazoles used as starting substances are prepared as described above.

We claim:

1. A pharmaceutical composition for treatment of diseases caused by trichomonads and amebae, consisting essentially of an amount, effective against said trichomonads and amebae, an active compound of the formula

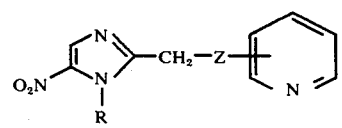

in which R stands for methyl, ethyl or hydroxyethyl and Z stands for —SO— or —SO$_2$— and the pyridine ring is linked to the sulfinyl or the sulfonyl group in 2, 3 or 4 position in admixture with a pharmaceutical carrier.

2. A composition as defined in claim 1 in which the active compound is 1-methyl-2-(2-pyridylsulfonylmethyl)-5-nitroimidazole.

3. An oral dosage unit for treatment of diseases caused by trichomonads and amebae consisting essentially of about 10 to 750 mg of an active compound of the formula

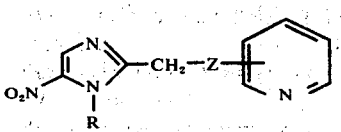

in which R stands for methyl, ethyl or hydroxyethyl and Z stands for —SO— or —SO$_2$— and the pyridine ring is linked to the sulfinyl or the sulfonyl group in 2, 3 or 4 position in admixture with a pharmaceutical carrier.

4. An oral dosage unit as defined in claim 3 in which the active compound is 1-methyl-2-(2-pyridylsulfonyl-methyl)-5-nitroimidazole.

5. Method of treatment of diseases caused by trichomonads and amebae which comprises orally administering to a patient a daily dosage of about 10 to 750 mg of an active compound as defined in claim 3.

6. Method of treatment as defined in claim 5 in which the active compound is 1-methyl-2-(2-pyridylsulfonyl-methyl)-5-nitroimidazole.

* * * * *